(12) United States Patent
Srinivasan et al.

(10) Patent No.: US 11,007,312 B2
(45) Date of Patent: May 18, 2021

(54) PEN NEEDLE MAGAZINE (71) Applicant: Becton, Dickinson and Company, Franklin Lakes, NJ (US)

(72) Inventors: Sudarsan Srinivasan, North Brunswick, NJ (US); Cole Constantineau, Cambridge, MA (US); Michel Bruehwiler, Newton, MA (US); Tyson Montidoro, Davie, FL (US); Jeffrey Chagnon, Somerville, MA (US); Daniel Yasevac, San Diego, CA (US); Chris Campbell, Somerville, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 249 days.

(21) Appl. No.: 16/094,358

(22) PCT Filed: Mar. 31, 2017

(86) PCT No.: PCT/US2017/025262
§ 371 (c)(1),
(2) Date: Oct. 17, 2018

(87) PCT Pub. No.: WO2017/189163
PCT Pub. Date: Nov. 2, 2017

(65) Prior Publication Data
US 2019/0117877 A1 Apr. 25, 2019

Related U.S. Application Data (60) Provisional application No. 62/328,654, filed on Apr. 28, 2016.

(51) Int. Cl.
*A61M 5/00* (2006.01)
*A61M 5/32* (2006.01)
*A61M 5/34* (2006.01)

(52) U.S. Cl.
CPC .......... *A61M 5/002* (2013.01); *A61M 5/3202* (2013.01); *A61M 5/322* (2013.01);
(Continued)

(58) Field of Classification Search
CPC .. A61M 5/002; A61M 5/3202; A61M 5/3204; A61M 5/322; A61M 5/3298;
(Continued)

(56) References Cited

U.S. PATENT DOCUMENTS 5,829,589 A   11/1998   Nguyen et al.
5,873,462 A    2/1999   Nguyen et al.
(Continued)

FOREIGN PATENT DOCUMENTS

EP   2119423 A1   11/2009
EP   2420270 A2    2/2012
(Continued)

OTHER PUBLICATIONS

Li-Yuan Chang et al., "Integrated Flow Sensing for Focal Biochemical Stimulation", Proceedings of the Third IEEE International Conference on Nano/Micro Engineered and Molecular Systems, Jan. 6-9, 2008, Sanya, China, pp. 921-926, (6 Pages Total).

*Primary Examiner* — Bhisma Mehta
*Assistant Examiner* — John J Crawford
(74) *Attorney, Agent, or Firm* — Dickinson Wright PLLC (57) ABSTRACT

An attachable needle assembly (2) used on a medication delivery pen (4), the needle assembly (2) comprising a spike (9) configured to pierce a vial, reservoir or cartridge septum of the pen (4), a needle guide (12) configured to mate with the pen (4), the needle guide (12) enclosing a septum (22) of the needle assembly (2) defining a septum chamber (31), the septum chamber (31) being in fluid communication with the spike (9), a plurality of needles (34) disposed in the septum (22) of the needle assembly (2), a sterility barrier (60)

(Continued)

enclosing each of the plurality of needles (34), each of a plurality of sterility barriers (60) having a peel tab (70), each of a plurality of peel tabs (70) being wrapped around the needle guide (12), wherein when one of the plurality of needles (40) is drawn from the needle guide (12) from a first position to a second position, the needle (40) fluidly communicates with the septum chamber (31), and the sterility barrier (60) and the peel tab (70) of the needle (40) are removed.

20 Claims, 12 Drawing Sheets (52) U.S. Cl.
CPC ........... *A61M 5/3298* (2013.01); *A61M 5/345* (2013.01); *A61M 2005/004* (2013.01); *A61M 2005/342* (2013.01); *A61M 2205/273* (2013.01)

(58) Field of Classification Search
CPC ............ A61M 5/345; A61M 2005/004; A61M 2005/342; A61M 5/3213; A61M 5/3243; A61M 5/3295; A51M 2205/273
See application file for complete search history.

(56) References Cited

U.S. PATENT DOCUMENTS

| | | |
|---|---|---|
| 5,931,817 A | 8/1999 | Nguyen et al. |
| 8,876,780 B2 | 11/2014 | Bruehwiler et al. |
| 9,101,724 B2 | 8/2015 | Chapin et al. |
| 9,107,988 B2 | 8/2015 | Bruehwiler et al. |
| 9,155,838 B2 | 10/2015 | Bilton et al. |
| 9,381,303 B2 | 7/2016 | Abhijitsinh et al. |
| 9,717,860 B2 | 8/2017 | Bruehwiler et al. |
| 10,029,042 B2 | 7/2018 | Searle et al. |
| 2001/0014792 A1 | 8/2001 | West et al. |
| 2002/0020646 A1 | 2/2002 | Groth et al. |
| 2002/0020647 A1 | 2/2002 | Groth |
| 2005/0084631 A1 | 4/2005 | Anderson |
| 2008/0312604 A1 | 12/2008 | Boesen |
| 2010/0217206 A1 | 8/2010 | Lum et al. |
| 2011/0068034 A1 | 3/2011 | Hwang et al. |
| 2012/0004620 A1 | 1/2012 | Spool et al. |
| 2012/0016315 A1 | 1/2012 | Radmer et al. |
| 2012/0041373 A1* | 2/2012 | Bruehwiler ........... A61M 5/002 604/173 |
| 2012/0041381 A1* | 2/2012 | Raj ........................ A61M 5/002 604/192 |
| 2012/0041383 A1 | 2/2012 | Bruehwiler et al. |
| 2012/0041390 A1* | 2/2012 | Spool .................. A61M 5/3205 604/240 |
| 2013/0041321 A1 | 2/2013 | Cross et al. |
| 2013/0053751 A1 | 2/2013 | Holtham |
| 2014/0076758 A1 | 3/2014 | Dasbach et al. |
| 2014/0123479 A1 | 5/2014 | Dasbach |
| 2014/0262884 A1 | 9/2014 | Priebe et al. |
| 2014/0299622 A1 | 10/2014 | Hofmann et al. |
| 2014/0339113 A1 | 11/2014 | Hofmann et al. |
| 2015/0025469 A1 | 1/2015 | Larsen et al. |
| 2015/0163898 A1 | 6/2015 | Mokhtarzad |
| 2015/0335827 A1 | 11/2015 | Stefansen et al. |
| 2015/0346184 A1 | 12/2015 | Galasso |
| 2016/0000992 A1 | 1/2016 | Steel et al. |
| 2016/0030683 A1 | 2/2016 | Taylor et al. |
| 2016/0074587 A1 | 3/2016 | Searle et al. |
| 2016/0082195 A1 | 3/2016 | Atterbury et al. |
| 2016/0106925 A1 | 4/2016 | Boesen |
| 2017/0304556 A1* | 10/2017 | Carpenter ............. A61M 5/002 |

FOREIGN PATENT DOCUMENTS

| | | |
|---|---|---|
| EP | 2586475 A1 | 5/2013 |
| EP | 2696913 B1 | 9/2015 |
| WO | 2008/150715 A1 | 12/2008 |
| WO | 2014/020001 A1 | 2/2014 |
| WO | 2016/050902 A1 | 4/2016 |

\* cited by examiner

PEN NEEDLE MAGAZINE

This application claims the benefit under 35 U.S.C. § 119(e) of U.S. Provisional Patent Application Ser. No. 62/328,654, filed on Apr. 28, 2016, which is hereby incorporated by reference in its entirety.

FIELD

Various exemplary embodiments of the invention relate to medication pens.

BACKGROUND

Medication pens are typically used to inject medication into a patient. A person who must periodically self-inject doses of medication will typically carry a medication pen and several single-use pen needles. A medication pen is designed for safety and sterility. However, inefficiencies and inconveniences arise.

SUMMARY OF THE INVENTION

It is an aspect of the present invention to provide a needle assembly that is attachable to a medication delivery pen to provide a magazine of needles for use. Such a needle assembly provides advantages in separating a patient end and a non-patient end, and allows for engagement and disengagement to the medication delivery pen. Moreover, improvements in sterility, simplicity and safety are achieved by the needle assembly because none of the needles in the magazine pierce the septum of the medication delivery pen throughout operation, each needle only moves axially, and the needles are unable to be reused.

Having a magazine of needles available for medication delivery reduces needle reuse. Needle reuse is undesired for at least the following reasons. The needle dulls after a single use and so subsequent use may cause pain to the patient. Multiple needle use can also reduce the strength of the needle tip which may cause a potential fracture. Also, needle reuse increases sanitary concerns and health risks to the patient.

The needle assembly of the present invention advantageously reduces reuse for at least the following reasons. Although patients may desire to financially benefit from using a needle multiple times, the needle assembly is configured to prevent each of the plurality of needles from being used more than once. Convenience is another reason patients reuse needles. Patients may also be concerned about not having another needle available for use or not having access to supplies. However, the needle assembly conveniently provides multiple needles so that an unused needle is more readily available.

The foregoing and/or other aspects of the present invention can be achieved by providing an attachable needle assembly for use on a medication delivery pen, the needle assembly comprising a spike that is configured to pierce a vial, cartridge or reservoir septum of the medication delivery pen, a needle guide secured to the spike and configured to engage the medication delivery pen, the needle guide enclosing a septum of the needle assembly defining a septum chamber, the septum chamber of the needle assembly being in continuous fluid communication with the spike, a plurality of needles disposed in the septum of the needle assembly, a sterility barrier enclosing each of the plurality of needles, each of a plurality of sterility barriers having an integrated peel tab, each of a plurality of integrated peel tabs being wrapped around a portion of the needle guide, wherein when one of the plurality of needles is drawn out of the needle guide for use from a first position to a second position, the needle enters into fluid communication with the septum chamber of the needle assembly, and the sterility barrier and the integrated peel tab of the needle are removed to expose the needle.

The foregoing and/or other aspects of the present invention can also be achieved by a method of operating an attachable needle assembly on a medication delivery pen, the method comprising piercing a vial, cartridge or reservoir septum of the medication delivery pen with a spike, engaging the medication delivery pen with a needle guide that is secured to the spike, establishing fluid communication between the spike and a septum chamber, disposing a plurality of needles in the septum of the needle assembly, enclosing each of the plurality of needles with a sterility barrier, providing an integrated peel tab to each of a plurality of sterility barriers, and wrapping each of a plurality of integrated peel tabs around a portion of the needle guide, wherein when one of the plurality of needles is drawn out of the needle guide for use from a first position to a second position, the needle enters into fluid communication with the septum chamber of the needle assembly, and the sterility barrier and the integrated peel tab of the needle are removed to expose the needle.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which.

DETAILED DESCRIPTION OF EXEMPLARY EMBODIMENTS

Figure 1:
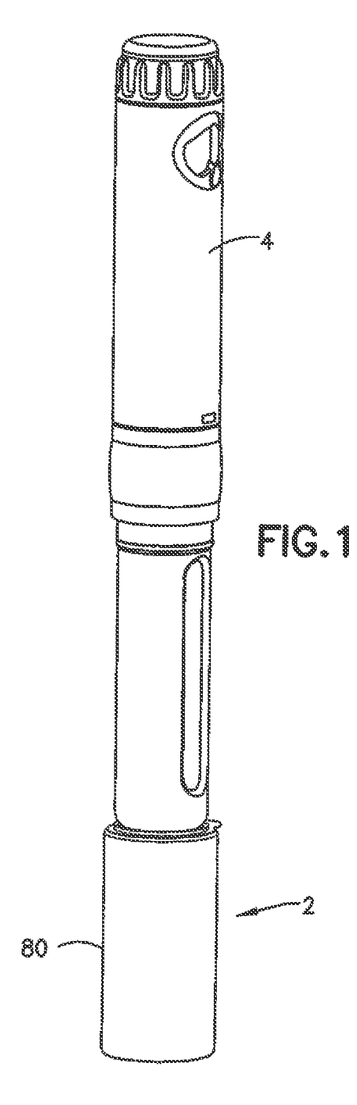
FIG. 1 illustrates a right perspective view of an exemplary medication delivery pen connected to a needle assembly.
Figure 2:
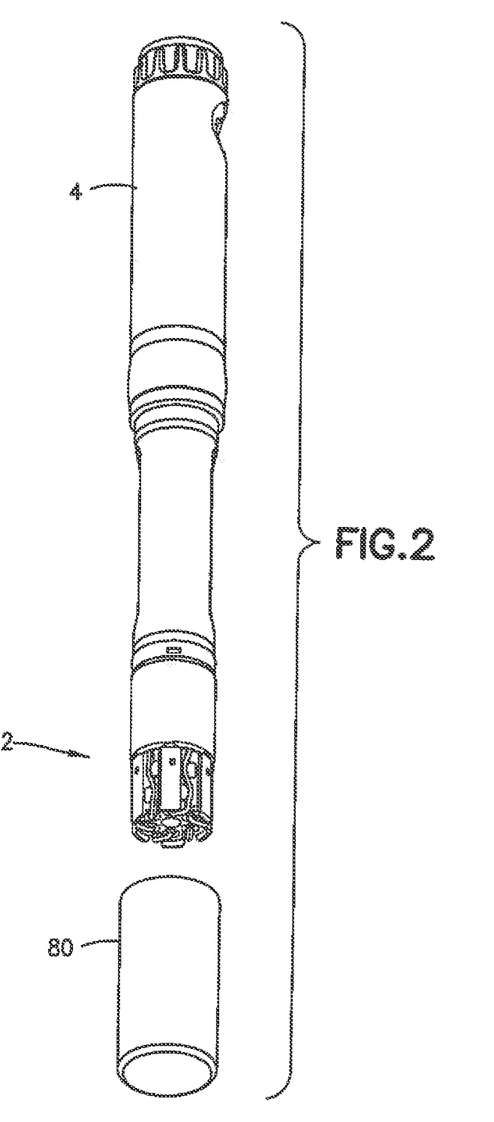
FIG. 2 illustrates a right perspective view of a medication delivery pen connected to a needle assembly with a cover removed.

FIG. 1 illustrates a medication delivery pen 4 used for injecting medicament, such as liquid drugs, into a living body. A needle assembly 2 is mounted on the medication delivery pen 4 to enhance medication delivery. Benefits and advantages of the needle assembly 2 are described below. FIG. 2 illustrates a removable cover 80 that encloses the needle assembly 2. The features of the removable cover 80 will also be described in detail below.

Figure 3:
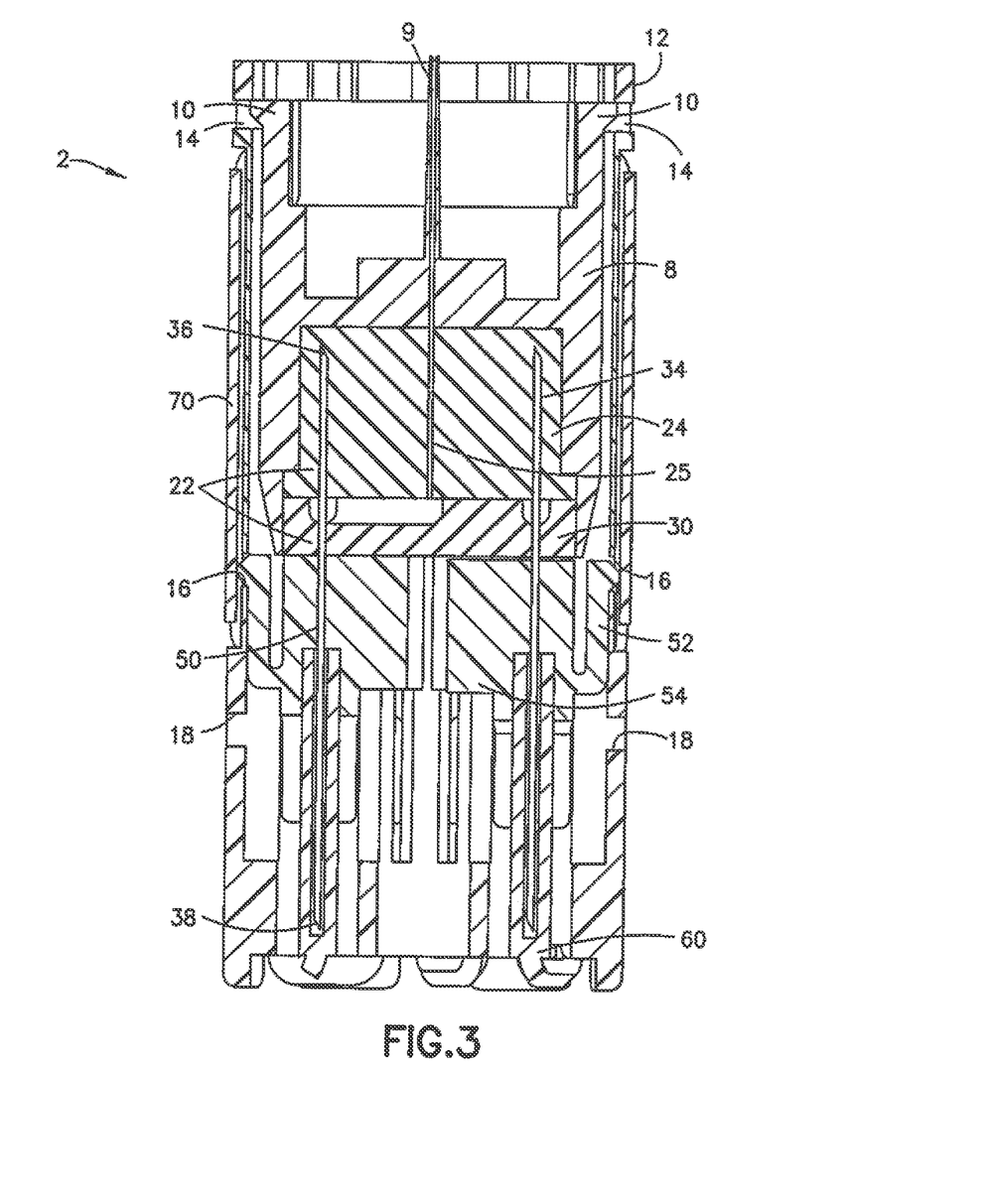
FIG. 3 illustrates a cross sectional view of a first position of the needle assembly.

According to one embodiment, FIG. 3 illustrates a cross sectional view of a first position of the needle assembly 2 where none of a plurality of needles 34 are exposed for medicament delivery. The needle assembly 2 preferably includes a magazine of seven hollow needles, although greater or fewer needles are contemplated. The needle assembly 2 includes a spike housing 8 with a spike 9 and two spike flanges 10. The spike housing 8 is disposed in a needle guide 12. The spike housing 8 is configured to engage the medication delivery pen 4. For example, an inner wall of the spike housing 8 can be threaded to engage with threads on the medication delivery pen 4. Various other engagement means are contemplated. The spike 9 is configured to pierce a vial, cartridge or reservoir septum (not shown), for example, of the medication delivery pen 4 and establish fluid communication between a liquid medication-containing vial, cartridge or reservoir and the needle assembly 2. The two spike flanges 10 are configured to engage the needle guide 12 to secure the spike housing 8 to the needle assembly 2. The needle guide 12 includes openings 14 that receive the spike flanges 10 to secure the spike 8 to the needle guide 12.

Figure 12:
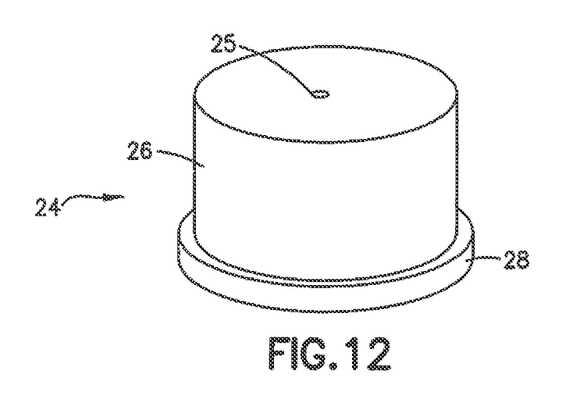
FIG. 12 illustrates a front perspective view of an upper septum.

The needle assembly 2, according to one embodiment, further includes a needle assembly septum 22. The needle assembly septum 22 includes an upper septum 24 and a lower septum 30. The upper septum 24 is disposed within the spike housing 8, As illustrated in FIG. 12, the upper septum 24 includes an upper septum hole 25 that travels through the upper septum 24 at its centerline. The upper septum hole 25 communicates with the spike 9 of the spike housing 8 to allow liquid medicament to flow into the needle assembly 2. The upper septum 24 includes a first diameter portion 26 and a second diameter portion 28 where the first diameter portion 26 is smaller in diameter than the second diameter portion 28. Both the first and second diameter portions 26, 28 are disposed in the spike housing 8.

Figure 13:
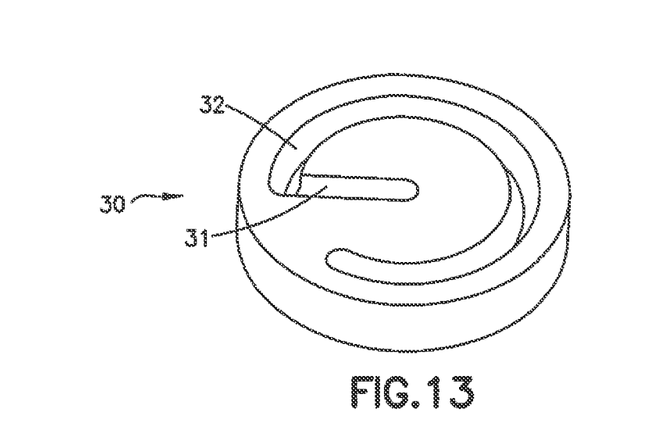
FIG. 13 illustrates a front perspective view of a lower septum.

FIG. 13 illustrates the lower septum 30 including a septum chamber comprising a continuous circular cavity 32 and a longitudinal cavity 31. The continuous circular cavity 32 or a curved recess is disposed on a top face of the lower septum 30. The circular cavity 32 continuously extends approximately 315°±30° around the top face of the lower septum 30 and adjacent to a circumferential edge of the lower septum 30. At one end point of the circular cavity 32, the longitudinal cavity 31 or longitudinal recess extends toward a center of the lower septum 30. In assembly, the top face of the lower septum 30 is in direct sealing contact with the second diameter portion 28 of the upper septum 24. The upper septum 24 and the lower septum 30 are preferably composed of different materials having different durometers. Such characteristics enhance sealing between the top face of the lower septum 30 and the second diameter portion 28 of the upper septum 24. The longitudinal cavity 31 of the lower septum 30 establishes fluid communication with the upper septum hole 25 and the spike 9 to fill the septum chamber with medicament.

According to one embodiment, the needle assembly 2 also includes a plurality of needles 34 that pierce the needle assembly septum 22. In the first position of the needle assembly 2, all of the plurality of needles 34 pierces the upper and lower septums 24, 30 and none of the needles are exposed. A proximal end 36 of each of the plurality of needles 34 is disposed in the upper septum 24 providing needle sterility. In the second position of the needle assembly 2, at least one of the plurality of needles 34 is exposed for medicament delivery. A proximal end of the selected needle is disposed in the circular cavity 32 of the lower septum 30 to receive medicament. The second position of the needle assembly 2 is described in more detail below. The plurality of needles 34 includes six needles, although greater or fewer needles are contemplated.

Figure 14:
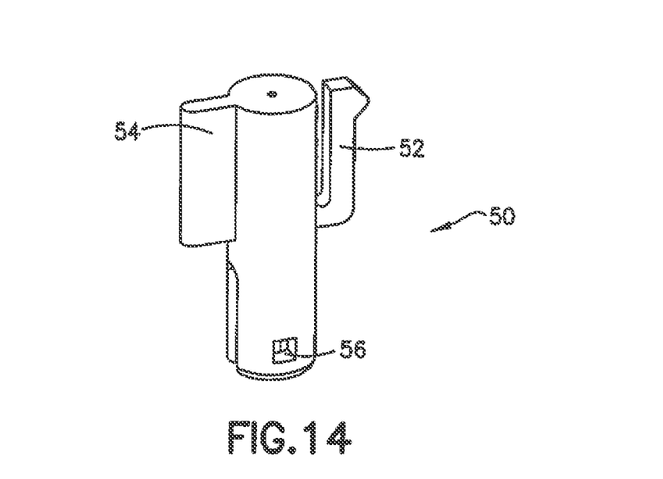
FIG. 14 illustrates a right perspective view of a needle post.
Figure 15:
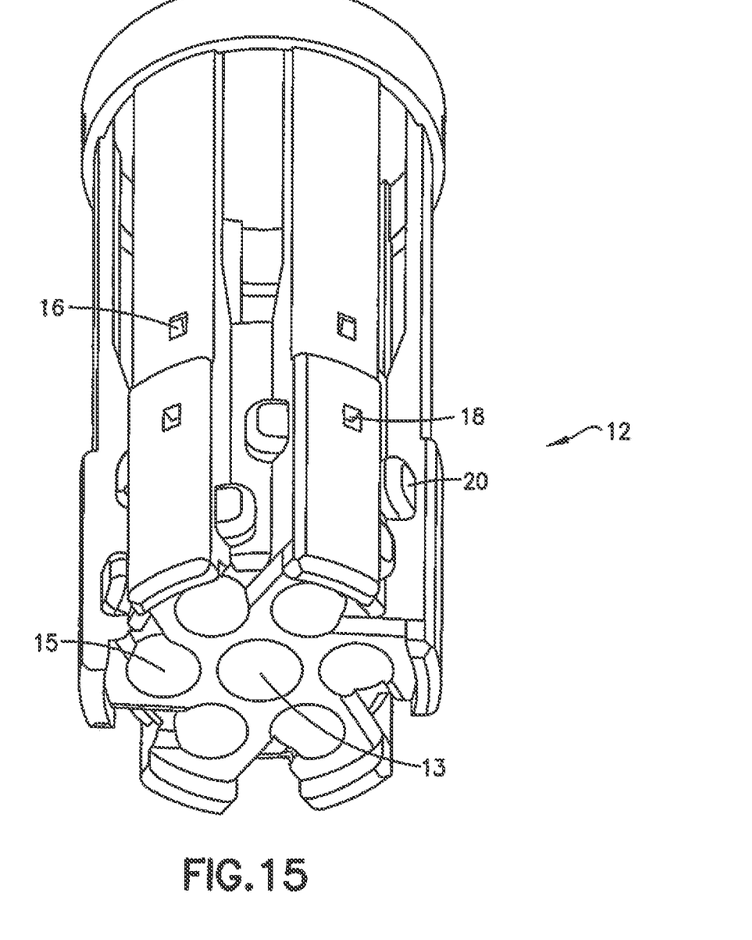
FIG. 15 illustrates a left perspective view of a needle guide.

Each of the plurality of needles 34 is fixed to a needle post 50. According to one embodiment, FIG. 14 illustrates the needle post 50 including a needle post flange 52, a needle post extension 54 and a sterility barrier opening 56. The needle post flange 52 provides a means to secure the needle post flange 52 to the needle guide 12. As illustrated in FIGS. 3 and 15, the needle guide 12 includes first needle post openings 16 and second needle post openings 18. The first and second needle post openings 16, 18 of the needle guide 12 engage the needle post flange 52 of the needle post 50 to secure the needle post 50 between the top and bottom positions. Specifically, in the first position of the needle assembly 2, the first needle post openings 16 are engaged with the needle post flange 52. In the second position of the needle assembly 2, the second needle post openings 18 are engaged with at least one needle post flange 52.

The needle post extension 54 allows the needle post 50 to retract the needle from the second position of the needle assembly 2 to the first position. The sterility barrier opening 56 engages a sterility barrier 60 to secure the sterility barrier 60 to the needle post 50. These features are described in further detail below.

According to one embodiment, a sterility barrier 60 is disposed at a sharpened distal end 38 of each of the plurality of needles 34 in the first position of the needle assembly 2. The plurality of sterility barriers 60 stores each of the needles 34 in a sterile environment prior to use and improves safety by protecting a user from inadvertent contact.

Figure 4:
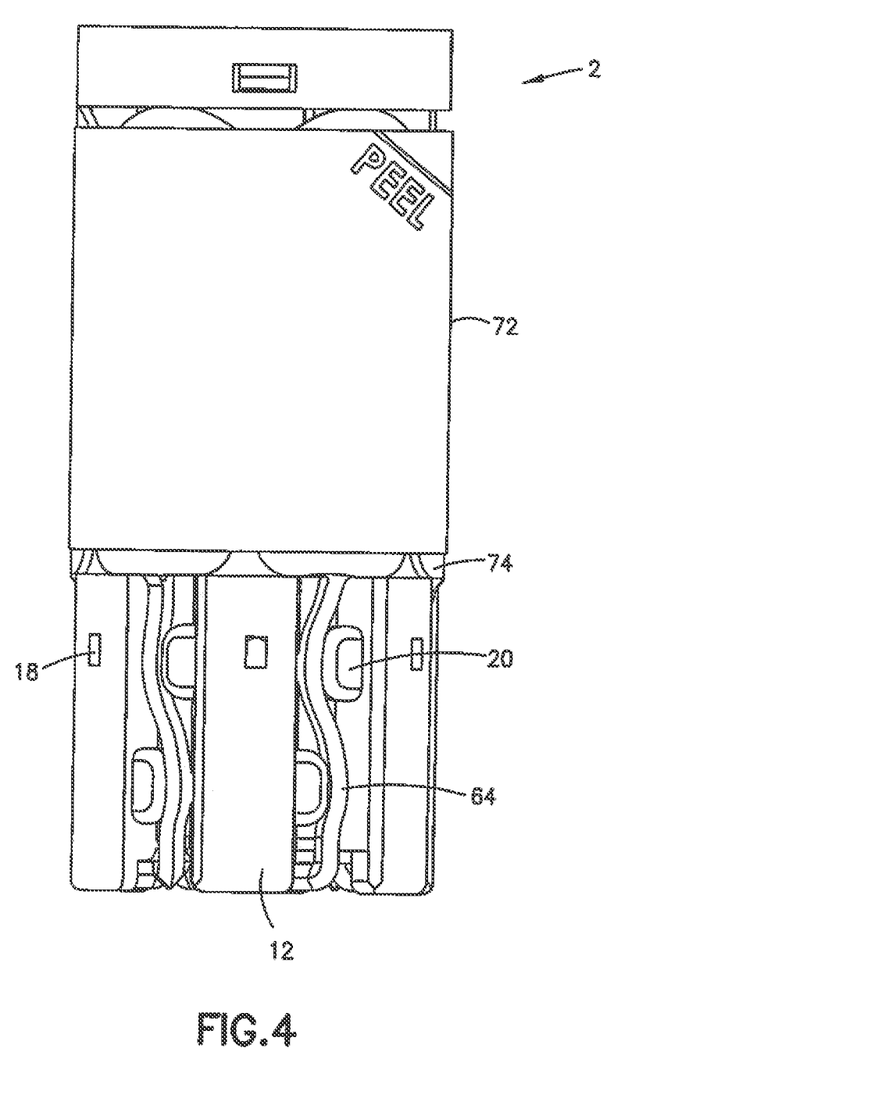
FIG. 4 illustrates a left side elevation view of the first position of the needle assembly.
Figure 16:
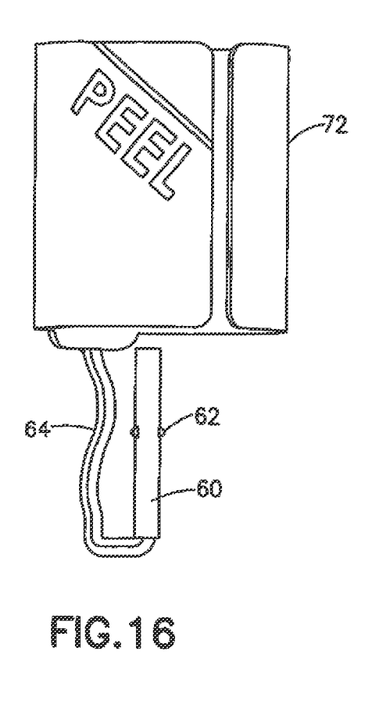
FIG. 16 illustrates a front elevation view of a large peel tab.
Figure 17:
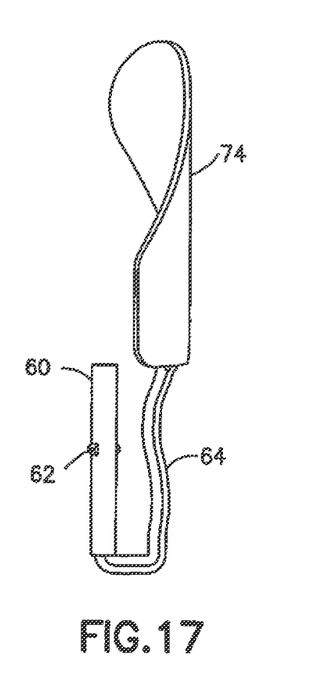
FIG. 17 illustrates a left side elevation view of a small peel tab.

According to one embodiment, FIGS. 16 and 17 illustrate that each of the plurality of sterility barriers 60 includes a foil wire, wire, wire with a paper laminate over it, plastic strip, or fabric string 64 that connects to an integrated peel tab 70. The foil wire 64 is the preferred embodiment but any material strong enough to withstand the forces involved in removing the sterility barrier 60 with the needle 34 is suitable. As illustrated in FIG. 4, the foil wire 64 wraps around the needle guide 12. Specifically, the needle guide 12 include obstructions 20 that slightly compress the wire 64 to secure the sterility barrier 60 and the integrated peel tabs 70.

The sterility barriers 60 also include a locking protrusion 62 that engages the sterility barrier opening 56 of the needle post 50 as described above.

The integrated peel tabs 70 include one large peel tab 72 and a plurality of small peel tabs 74. The large peel tab 72 is greater in surface area than the small peel tab 74. Preferably, the needle assembly 2 includes one large peel tab 72 and six small peel tabs 74. The plurality of small peel tabs 74 are wrapped around various portions of the needle guide 12 as illustrated in FIGS. 4-6 and 8. Specifically, the plurality of needles 34 are consecutively arranged such that a portion of the respective peel tabs 74 lies underneath the subsequent needle. After all the small peel tabs 74 are arranged, the large peel tab 72 is disposed above all the small peel tabs 74. The large peel tab 72 is connected to the first needle of the plurality of needles 34. In this manner, the first needle of the plurality of needles 34 is used first so that the needle assembly septum 22 is properly primed as further described below.

Figure 5:
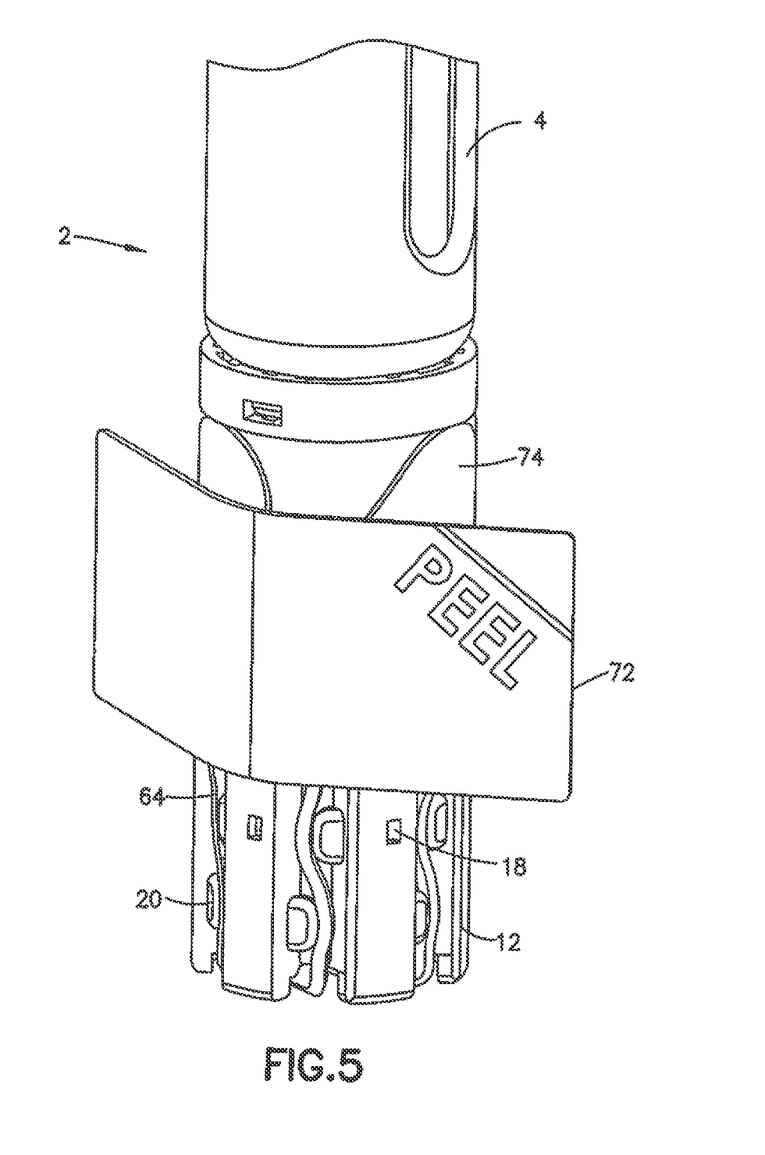
FIG. 5 illustrates a front side elevation view of the first position of the needle assembly with a peel tab being removed.
Figure 6:
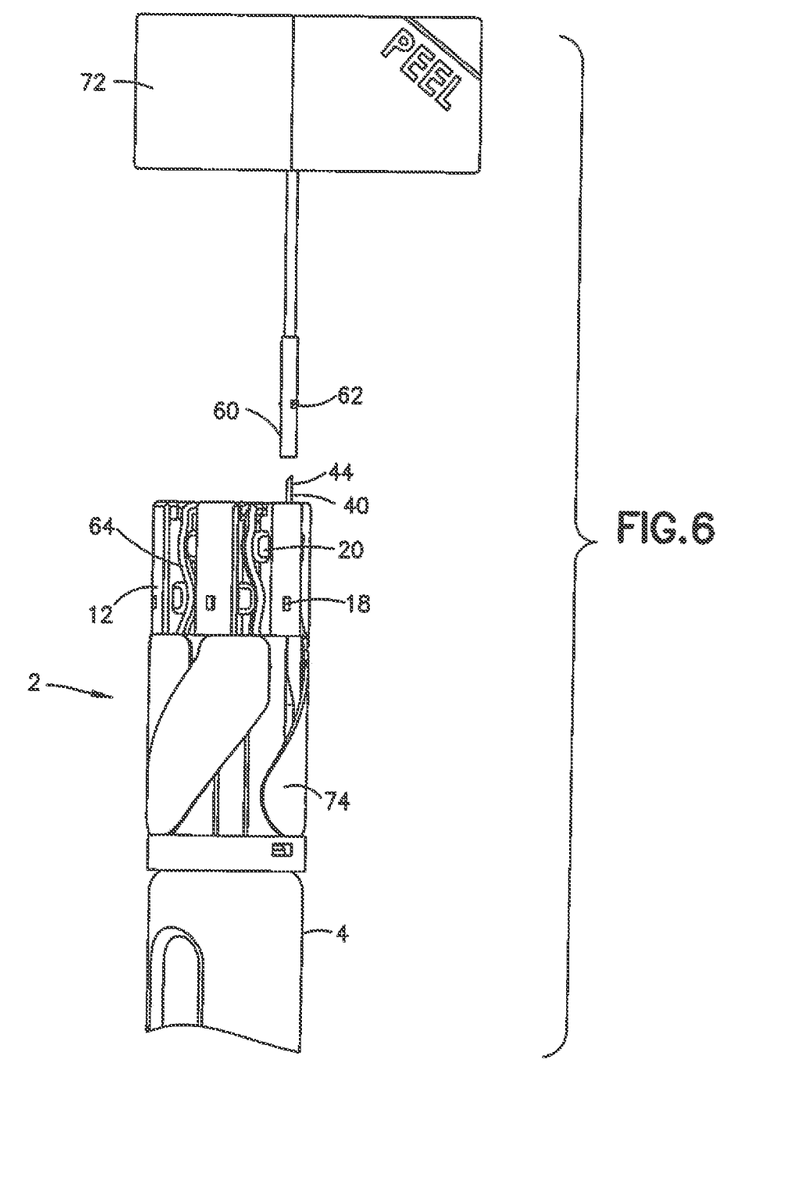
FIG. 6 illustrates a left side elevation view of a second position of the needle assembly.

The operation of the needle assembly 2 is now explained as follows. According to one embodiment, when the user desires to connect the needle assembly 2 to the medication delivery pen 4 for use, the large peel tab 72 is removed first as illustrated in FIG. 5. Since the large peel tab 72 is disposed above all the small peel tabs 74, the user must remove the large peel tab 72 first. Accordingly, the arrangement of the plurality of integrated peel tabs 70 determines the order of operation for each of the plurality of needles 34.

After the large peel tab 72 is removed, a selected needle 40 and the associated sterility barrier 60 are drawn out of the needle guide 12. When the selected needle 40 is fully drawn out, the needle assembly 2 is in the second position. Subsequently, the sterility barrier 60 is removed from the selected needle 40 and the needle assembly 2 is ready for medicament delivery.

Figure 7:
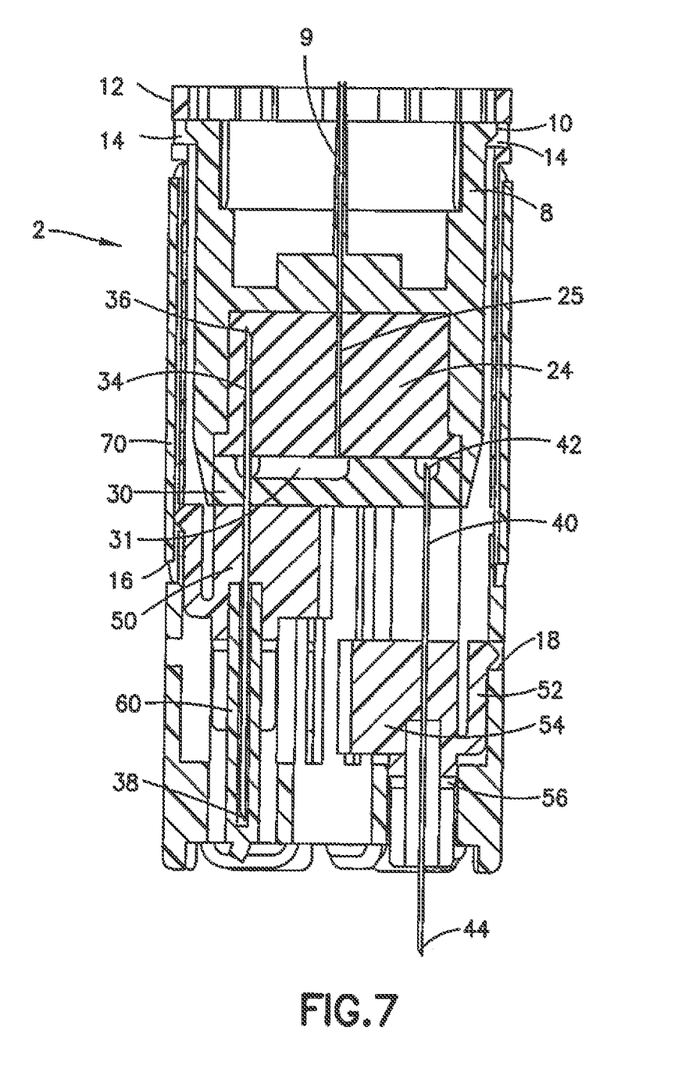
FIG. 7 illustrates a cross sectional view of the second position of the needle assembly.

According to one embodiment, FIG. 7 illustrates the selected needle 40 in the second position of the needle assembly 2. The needle post 50 of the selected needle 40 moves from the top position to the bottom position. Specifically, the top position is where the needle post flange 52 engages the first needle post opening 16 of the needle guide 12, and the bottom position is where the needle post flange 52 engages the second needle post opening 18 of the needle guide 12.

When the needle assembly 2 is in the second position, the distal end 44 of the selected needle 40 is exposed for medication delivery. A proximal end 42 of the selected needle 40 enters into the circular cavity 32 of the lower septum 30 and establishes fluid communication with the medicament in the circular cavity 32. Accordingly, medicament is received by the selected needle 40 and exits the distal end 44 to be delivered to a patient.

When the first needle of the plurality of needles 34 is used, the circular cavity 32 is filled with medicament, resulting in the needle assembly septum 22 being primed. Specifically, medicament must traverse and fill the complete fluid path of the circular cavity 32 to reach the first needle of the plurality of needles 34. Accordingly, the incidence of air in the circular cavity 32 is advantageously reduced. Removing air from the fluid path also advantageously improves dose accuracy.

While the needle assembly 2 is in the second position, a remaining plurality of needles 34 (not including the selected needle 40) and the associated needle post 50 remains in the top position. Specifically, the proximal ends 36 of the remaining plurality of needles 34 are sealed in the upper septum 24. The remaining needles 34 are not in fluid communication with the medicament stored in the circular cavity 32 of the lower septum 30. However, some portion of each of the remaining needles 34 contacts the medicament because these remaining needles 34 are aligned with the circular cavity 32 of the lower septum 30. The distal ends 38 of the remaining plurality of needles 34 are covered by the sterility barrier 60.

Figure 8:
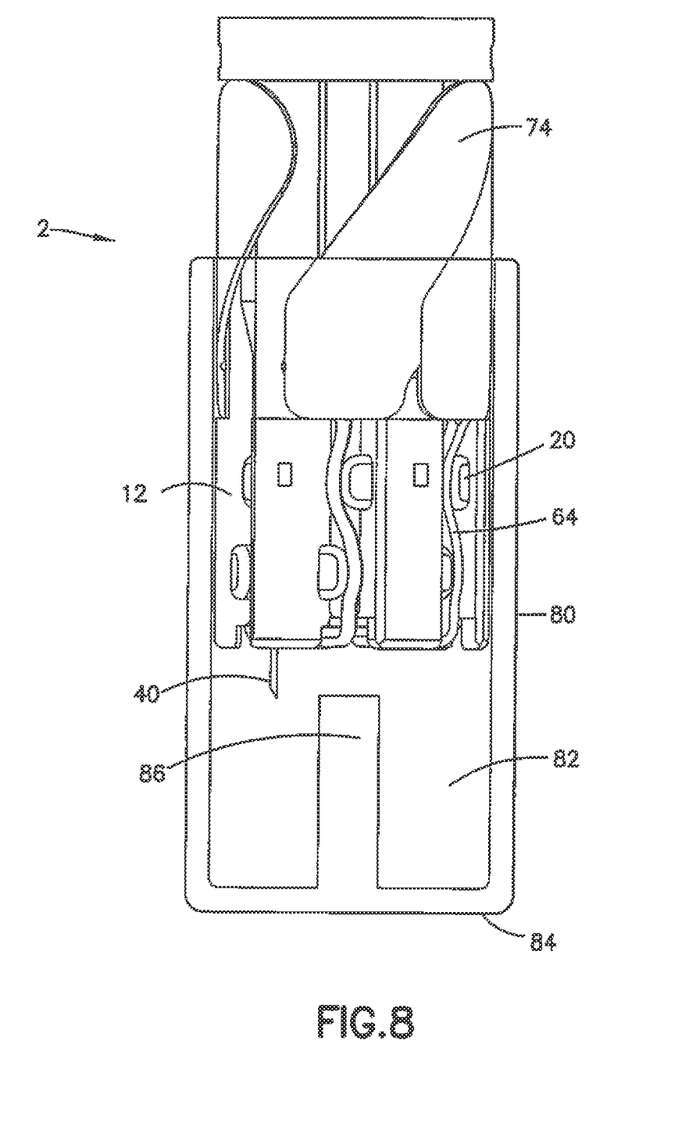
FIG. 8 illustrates a transparent front side elevation view of the second position of the needle assembly with the cover beginning to engage the needle assembly.

According to one embodiment, FIG. 8 illustrates the cover 80 used to move the needle assembly 2 from the second position to the first position. The cover 80 includes a cylinder 82, a base 84 and a protrusion 86. The cylinder 82 surrounds the needle assembly 2. The base 84 covers a bottom portion of needle guide 12 of the needle assembly 2. The protrusion 86 extends from the base 84 and is disposed centrally within the cylinder 82. When the cover 80 is placed on the needle assembly 2, the protrusion 86 applies pressure by pushing the needle post extension 54 of the needle post 50 of the selected needle 40 from the bottom position to the top position.

Figure 9:
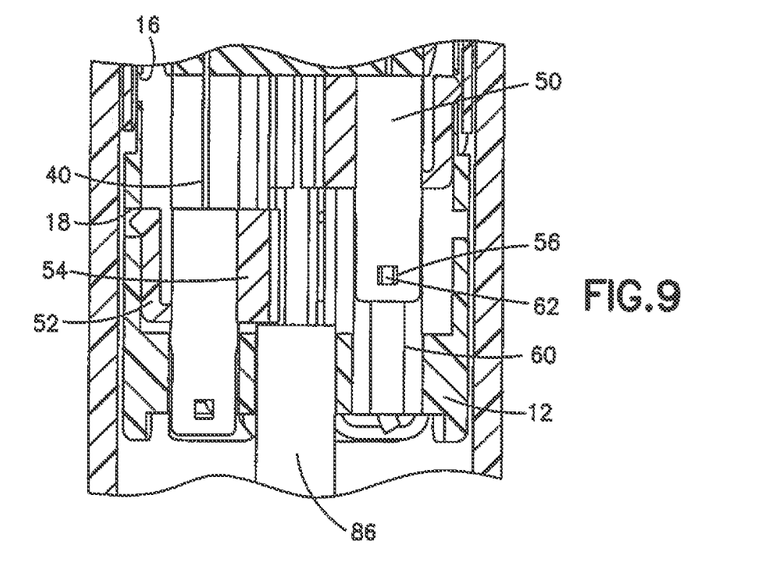
FIG. 9 illustrates a partial cross sectional view of a needle post assembly in the second position of the needle assembly.
Figure 10:
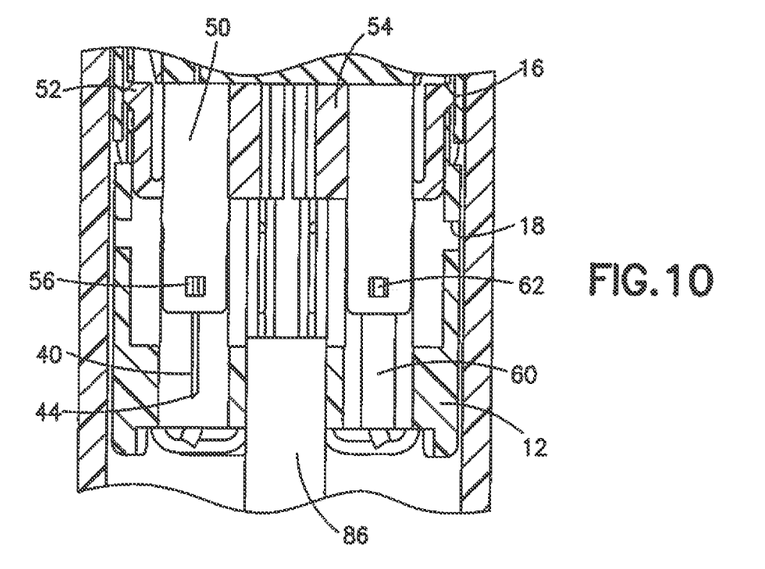
FIG. 10 illustrates a partial cross sectional view of a needle post assembly in the first position of the needle assembly.
Figure 11:
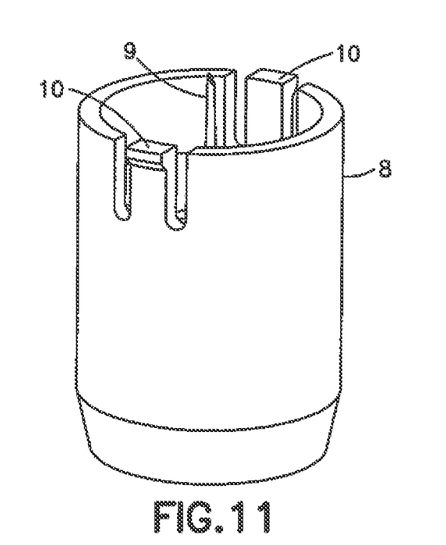
FIG. 11 illustrates a front perspective view of a spike.

According to one embodiment, FIGS. 9 and 10 illustrate the protrusion 86 of the cover 80 moving the needle post 50 by applying pressure to the needle post extension 54. FIG. 9 illustrates the second position of the needle assembly 2 and FIG. 10 illustrates the first position of the needle assembly 2. These figures also illustrate that the needle post extensions 54 of each of the plurality of needles 34 are arranged toward a central axis of the needle guide 12. Such a configuration advantageously allows the protrusion 86 of the cover 80 to engage each of the needle posts 50.

FIG. 15 illustrates the needle guide 12 including a cover hole 13 and a plurality of needle post holes 15. Each of the plurality of needle posts 50 travel through respective needle post holes 15 when moving between the top position and the bottom position. The cover hole 13 accommodates the protrusion 86 of the cover 80. Accordingly, the protrusion 86 of the cover 80 is configured to contact each of the needle post extensions 54 of the needle posts 50 for each successive use of the plurality of needles 34.

According to one embodiment, after the needle assembly 2 is returned to the first position, as illustrated in FIG. 10, the selected needle 40 can no longer be used. Since the selected needle 40 is no longer covered by the sterility barrier 60 and wrapped around the needle guide 12 by the integrated peel tab 70, the user cannot reuse the needle by pulling the selected needle 40 from the top position to the bottom position of the respective needle post 50.

After the needle assembly 2 is returned to the first position, according to one embodiment, an adjacent needle is selected for use. Specifically, as illustrated in FIG. 8, the plurality of small peel tabs 74 are arranged such that one small peel tab 74 lies on top of an adjacent small peel tab 74 when traveling clockwise according to a bottom view perspective of the needle assembly 2. As a result, the needle adjacent to the selected needle 40 in the clockwise direction is the next needle to be used. The needle adjacent to the selected needle is used by removing the small peel tab 74, pulling the needle from the first position to the second position of the needle assembly 2 and removing the sterility barrier 60 as described above. Subsequently, the cover 80 is used to return the selected needle to the first position of the needle assembly 2 and a next adjacent needle is ready for use. These steps are repeated until all the needles 34 are used.

According to an alternate embodiment, one small peel tab 74 lies on top of an adjacent small peel tab 74 when traveling counterclockwise according to a bottom perspective view of the needle assembly 2. Accordingly, the order of use of the needles is in a counterclockwise direction. During assembly, the order of use of the plurality of needles 34 can be determined by how the small peel tabs 74 are arranged with respect to each other.

According to one embodiment, when the needle assembly 2 is assembled, a small peel tab 74 of a first needle 34 is wrapped over the needle guide 12. A small peel tab 74 of an adjacent second needle 34 is wrapped on top of a portion of the small peel tab 74 of the first needle 34 and over a portion of the needle guide 12. This repeats for the first six needles. The seventh or last needle includes the large peel tab 72 that is wrapped over the majority of all the small peel tabs 74 and the needle guide 12. Accordingly, the user operates the needle assembly 2 by using the seven needles in the reverse order in which they were assembled on the needle guide 12 starting with the seventh needle.

During operation, although the selected needle 40 moves axially, the selected needle 40 does not move radially. In fact, none of the plurality of needles 34 substantially moves radially or rotates at any point during operation. No substantial radial or rotational movement in this regard is understood as 0±15% with respect to a center axis of the needle assembly 2. Preferably, one skilled in the art understands that substantial in this context means that no radial of rotational movement is required to perform the intended function. Slight radial or rotational movement is desired to ensure the proper spacing of parts for smooth operation and proper movement of the needles axially without jamming.

Each of the plurality of needles 34 is advantageously isolated from the septum of the medication delivery pen 4 throughout the operation of the needle assembly 2. Such an arrangement advantageously provides simplicity in design, improves sterility and provides a separation between a patient end and a non-patient end.

Figure 18:
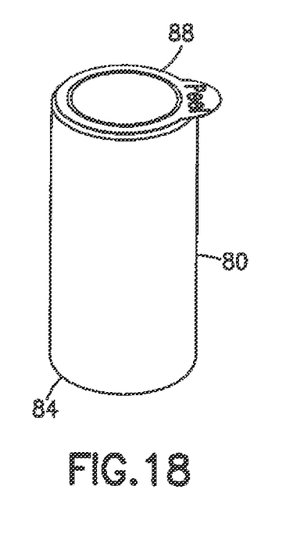
FIG. 18 illustrates a right perspective view of the needle assembly in a cover and sealed by a teardrop label.

According to one embodiment, FIG. 18 illustrates the cover 80 enclosing the needle assembly 2. The cover 80 is sealed with a teardrop label 88 to seal the needle assembly 2 and maintain its sterility for transportation and security purposes prior to operating with the medication delivery pen 4. When the needle assembly 2 is ready for use, the user peels off the teardrop label 88 and removes the needle assembly 2 from the cover 80.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed, as long as they do not contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with, manufacturing, assembly, and use of the described embodiments.

The invention claimed is:

1. An attachable needle assembly for use on a medication delivery pen, the needle assembly comprising:
    a spike that is configured to pierce a reservoir septum of the medication delivery pen;
    a needle guide secured to the spike and configured to engage the medication delivery pen, the needle guide enclosing:
        a septum of the needle assembly defining a septum chamber, the septum chamber of the needle assembly being in continuous fluid communication with the spike;
        a plurality of needles disposed in the septum of the needle assembly;
        a plurality of sterility barriers, each sterility barrier corresponding to and enclosing a needle of the plurality of needles, each sterility barrier corresponding to and having an integrated peel tab of a plurality of integrated peel tabs, each integrated peel tab being wrapped around a portion of the needle guide, wherein
    when a selected needle of the plurality of needles is drawn out of the needle guide for use from a first position to a second position, the selected needle enters into fluid communication with the septum chamber of the needle assembly, and the sterility barrier and the integrated peel tab of the selected needle are configured to be removed to expose the needle.

2. The attachable needle assembly of claim 1, wherein the plurality of integrated peel tabs includes at least one large peel tab and one small peel tab, the large peel tab is greater in surface area than the small peel tab.

3. The attachable needle assembly of claim 2, wherein the plurality of integrated peel tabs includes one large peel tab and six small peel tabs.

4. The attachable needle assembly of claim 1, wherein the septum of the needle assembly includes
    an upper septum that provides needle sterility; and
    a lower septum that provides fluid communication to the spike.

5. The attachable needle assembly of claim 4, wherein the lower septum includes the septum chamber comprising a circular cavity that carries medicament from the spike and fluidly communicates with the selected needle of the plurality of needles in the second position.

6. The attachable needle assembly of claim 4, wherein in the first position prior to operation, a proximal end of each needle of the plurality of needles is disposed in the upper septum and a distal end of each needle of the plurality of needles is disposed in the corresponding sterility barrier of the plurality of sterility barriers.

7. The attachable needle assembly of claim 4, wherein in the second position, a proximal end of the selected needle of the plurality of needles is disposed in the lower septum.

8. The attachable needle assembly of claim 4, wherein in the second position, a proximal end of each of a remaining plurality of needles is disposed in the upper septum.

9. The attachable needle assembly of claim 1, comprising a plurality of needle posts, wherein
    each of the plurality of needles is secured in a corresponding needle post of the plurality of needle posts; and the plurality of needle posts move in the needle guide and are engaged to the needle guide in a top position and a bottom position.

10. The attachable needle assembly of claim 1, wherein the plurality of needles do not pierce the reservoir septum of the medication delivery pen.

11. The attachable needle assembly of claim 1, wherein the plurality of needles only move axially and do not substantially move radially.

12. The attachable needle assembly of claim 1, further including
a cover enclosing the needle assembly; and
a label sealing and maintaining sterility of the needle assembly in the cover prior to operating with the medication delivery pen.

13. The attachable needle assembly of claim 1, wherein a cover is configured to apply pressure to the selected needle of the plurality of needles to return the selected needle from the second position to the first position.

14. The attachable needle assembly of claim 13, wherein the cover includes
a cylinder;
a base; and
a protrusion extending from the base and disposed within the cylinder, and the protrusion is configured to engage the needle guide to apply pressure to the selected needle of the plurality of needles to return the needle assembly from the second position to the first position.

15. The attachable needle assembly of claim 1, wherein when the selected needle of the plurality of needles returns from the second position to the first position of the needle assembly, the selected needle is unable to be reused.

16. The attachable needle assembly of claim 1, wherein each integrated peel tab is wrapped around an outer surface of the needle guide.

17. The attachable needle assembly of claim 1, wherein at least one of the plurality of integrated peel tabs contacts an outer surface of the needle guide.

18. An attachable needle assembly for use on a medication delivery pen, the needle assembly comprising:
a spike that is configured to pierce a reservoir septum of the medication delivery pen;
a needle guide secured to the spike and configured to engage the medication delivery pen, the needle guide enclosing:
a septum of the needle assembly defining a septum chamber, the septum chamber of the needle assembly being in continuous fluid communication with the spike;
a plurality of needles disposed in the septum of the needle assembly;
a plurality of sterility barriers, each sterility barrier corresponding to and enclosing a needle of the plurality of needles, each sterility barrier corresponding to and having an integrated peel tab of a plurality of integrated peel tabs, each integrated peel tab being wrapped around a portion of the needle guide, wherein
when a selected needle of the plurality of needles is drawn out of the needle guide for use from a first position to a second position, the selected needle enters into fluid communication with the septum chamber of the needle assembly, and the sterility barrier and the integrated peel tab of the selected needle are configured to be removed to expose the needle, wherein the plurality of integrated peel tabs includes at least one large peel tab and a plurality of small peel tabs, the large peel tab is greater in surface area than each of the plurality of small peel tabs; and
the large peel tab is wrapped over the plurality of small peel tabs.

19. An attachable needle assembly for use on a medication delivery pen, the needle assembly comprising:
a spike that is configured to pierce a reservoir septum of the medication delivery pen;
a needle guide secured to the spike and configured to engage the medication delivery pen, the needle guide enclosing:
a septum of the needle assembly defining a septum chamber, the septum chamber of the needle assembly being in continuous fluid communication with the spike;
a plurality of needles disposed in the septum of the needle assembly;
a plurality of sterility barriers, each sterility barrier corresponding to and enclosing a needle of the plurality of needles, each sterility barrier corresponding to and having an integrated peel tab of a plurality of integrated peel tabs, each integrated peel tab being wrapped around a portion of the needle guide, wherein
when a selected needle of the plurality of needles is drawn out of the needle guide for use from a first position to a second position, the selected needle enters into fluid communication with the septum chamber of the needle assembly, and the sterility barrier and the integrated peel tab of the selected needle are configured to be removed to expose the needle;
a first integrated peel tab of a first needle is wrapped over the needle guide;
at least a portion of a second integrated peel tab of an adjacent second needle is wrapped over the first integrated peel tab and the needle guide; and
a remaining plurality of integrated tabs is sequentially wrapped over an adjacent wrapped integrated peel tab to define the order of use upon operation.

20. A method of operating an attachable needle assembly on a medication delivery pen, the method comprising:
piercing a reservoir septum of the medication delivery pen with a spike;
engaging the medication delivery pen with a needle guide that is secured to the spike;
establishing fluid communication between the spike and a septum chamber of a septum of the needle assembly;
disposing a plurality of needles in the septum of the needle assembly;
enclosing each of the plurality of needles with a sterility barrier;
providing an integrated peel tab to each of the sterility barriers, and
wrapping each of the integrated peel tabs around a portion of the needle guide, wherein
when a selected needle of the plurality of needles is drawn out of the needle guide for use from a first position to a second position, the selected needle enters into fluid communication with the septum chamber of the septum of the needle assembly, and the sterility barrier and the integrated peel tab of the selected needle are removed to expose the needle.

* * * * *